United States Patent [19]

Sase et al.

[11] Patent Number: 4,680,627
[45] Date of Patent: Jul. 14, 1987

[54] APPARATUS FOR CHECKING PATTERNS ON PRINTED CIRCUIT BOARDS

[75] Inventors: Akira Sase, Katsuta; Takeo Nagata, Hitachi; Masao Fukunaga; Yutaka Sakurai, both of Katsuta; Yoshikatsu Satomi, deceased, late of Mito, by Fumiko Satomi, legal representative all of Japan

[73] Assignee: Hitachi, Ltd., Tokyo, Japan

[21] Appl. No.: 838,713

[22] Filed: Mar. 12, 1986

[30] Foreign Application Priority Data

Mar. 19, 1985 [JP] Japan ............................. 60-55205

[51] Int. Cl.⁴ .......................................... H06N 7/18
[52] U.S. Cl. .................................. 358/101; 356/394; 382/8; 382/45
[58] Field of Search ................... 358/101, 106, 107; 382/45, 8; 356/392, 393, 394, 398

[56] References Cited

U.S. PATENT DOCUMENTS

| 3,988,535 | 10/1976 | Hickman | 358/101 |
| 4,240,750 | 12/1980 | Kurtz | 356/394 |
| 4,319,845 | 3/1982 | Shuji | 356/394 |
| 4,334,241 | 6/1982 | Kashioka | 382/45 |
| 4,389,669 | 6/1983 | Epstein | 356/394 |
| 4,481,533 | 11/1984 | Alzmann | 358/101 |
| 4,614,430 | 9/1986 | Hara | 356/394 |

Primary Examiner—Howard W. Britton
Attorney, Agent, or Firm—Antonelli, Terry & Wands

[57] ABSTRACT

In an apparatus for checking patterns on printed circuit boards by comparing two patterns formed on two printed circuit boards, registration patterns each including orthogonal straight line segments and respectively formed on the two printed circuit boards are imaged by two imagers, and registration images from the imagers are matched by means of a registration unit to accurately match an image of a pattern to be checked on one printed circuit board with an image of a reference pattern on the other printed circuit board.

12 Claims, 12 Drawing Figures

FIG. 2
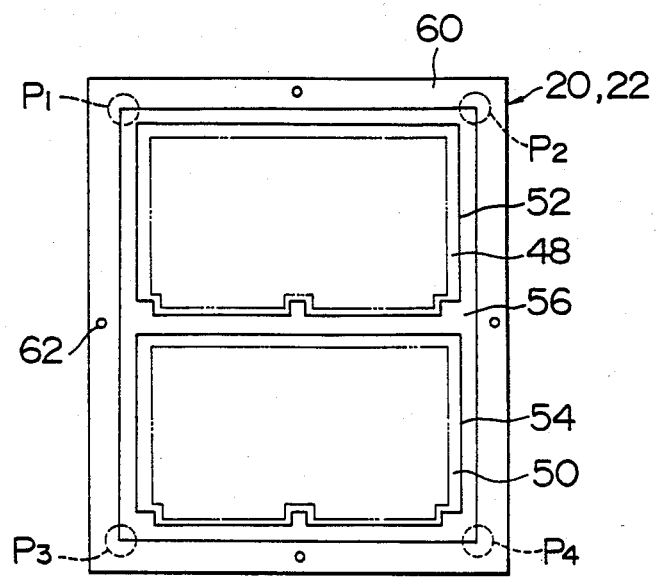
FIG. 3A         FIG. 3B
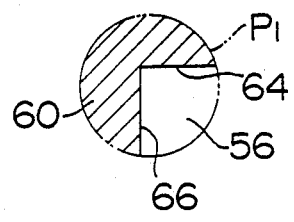    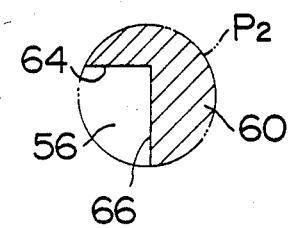

FIG. 6
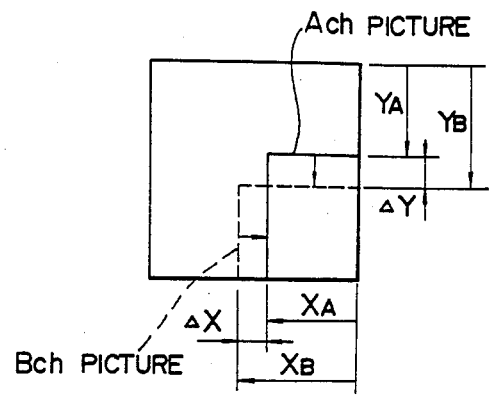
FIG. 7A    FIG. 7B    FIG. 7C
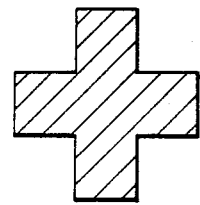 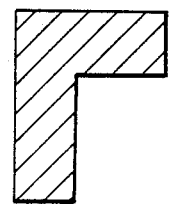 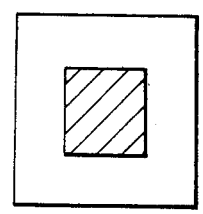

APPARATUS FOR CHECKING PATTERNS ON PRINTED CIRCUIT BOARDS

BACKGROUND OF THE INVENTION

This invention relates to an apparatus for checking patterns formed on printed circuit boards for use in an electronic apparatus and more particularly to a pattern checking apparatus for checking geometrical defects of a two-dimensional pattern by imaging the two-dimensional patterns and a two-dimensional reference pattern and comparing them with each other.

In recent years, high density packaging of the printed circuit board for use in electronic apparatus has drastically been advanced and consequently, development has been directed to enlargement of the printed circuit board and its formation into a multi-layer structure with fine patterns. Typically, a pattern formed on a printed circuit board is checked by imaging the pattern and a reference pattern formed on another circuit board and comparing them with each other. Because of fineness of these patterns, it is necessary that one printed circuit board carrying the reference pattern and the other to be checked for its pattern be accurately be held in predetermined positions and those patterns for comparison be imaged simultaneously. Conventionally, this type of checking apparatus based on pattern comparison has an inspection table provided, at predetermined positions, with guide pins, which are fitted in holes formed in the printed circuit boards to complete mounting of these boards to the inspection table.

By using these guide pins, the printed circuit boards can be positioned with a displacement of approximately 0.1 to 0.2 mm. Conventionally, since the printed circuit board has patterns of a relatively large width and the slight displacement in positioning can fall within a tolerance of the pattern width, checking can be accomplished with sufficient accuracies by positioning the boards through the use of guide pins. However, a printed circuit board, enlarged with an attendant decrease in thickness of its substrate, tends to have a dimensional error of about 0.1% which is due to such factors as working distortion caused by printed circuit board fabrication processes and thermal contraction attributable to temperature changes. In addition, because of fineness of patterns, a printed circuit board carrying patterns of a pattern width of about 0.1 mm has initially been practiced. For these reasons, a need of confining the accuracy for positioning within several of tens of microns arises and the conventional positioning based on only the guide pins can not meet the need. Further, conventionally, the two printed circuit boards to be compared to each other are positioned by manually adjusting images displayed on a CRT screen so as to match them and therefore, accurate positioning operations are very difficult to achieve.

SUMMARY OF THE INVENTION

An object of this invention is to provide an apparatus for checking patterns formed on printed circuit boards which can accurately match an image of a pattern on a printed circuit board with an image of a corresponding pattern on another printed circuit board which is compared to the former board.

This invention is grounded on the fact that if patterns on respective printed circuit boards are of a two-dimensional pattern which has orthogonal straight line portions, images of the patterns can be matched accurately by utilizing these orthogonal straight line portions. Thus, in a pattern checking apparatus according to the invention, registration patterns each including orthogonal straight line segments and respectively formed on two printed circuit boards compared to each other are imaged by two imagers, and registration images from the imagers are matched by means of a registration unit to accurately match an image of a pattern to be checked on one printed circuit board with an image of a reference pattern on the other printed circuit board, thereby making it possible to accurately compare the pattern to be checked with the reference pattern.

BRIEF DESCRIPTION OF THE DRAWINGS

FIG. 2 is a plan view showing an example of a printed circuit board;

FIGS. 3A and 3B are enlarged fragmentary views showing corners of the printed circuit board shown in FIG. 2;

FIG. 6 shows a combined image of the two histograms shown in FIGS. 5A and 5B; and FIGS. 7A to 7C are diagrams showing examples of registration marks.

DESCRIPTION OF THE PREFERRED EMBODIMENT

Figure 1:
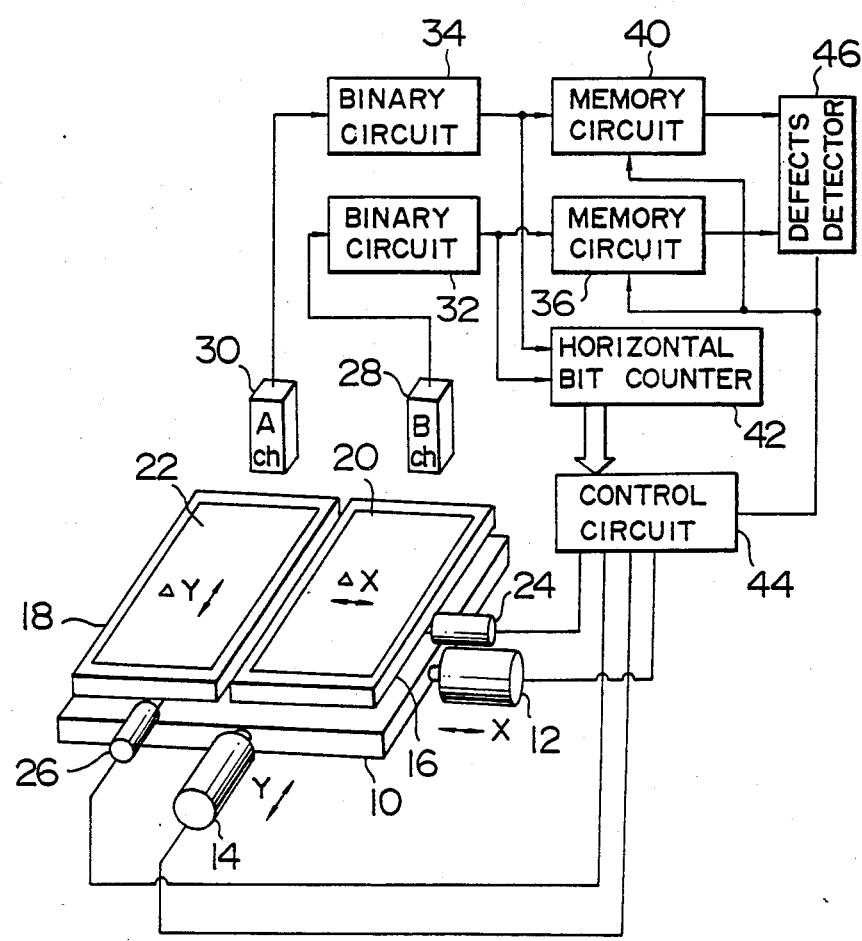
FIG. 1 is a block diagram showing an apparatus for checking patterns on printed circuit boards according to an embodiment of the invention.

Referring to FIG. 1 an XY table 10 serving as an inspection table is attached with drive motors 12 and 14 and movable in X directions (lateral directions in FIG. 1) and in Y directions orthogonal thereto. Slidably mounted on the XY table 10 are fine adjustment tables 16 and 18 serving as auxiliary tables on which printed circuit boards 20 and 22 are fixedly mounted, respectively. One of the boards 20 and 22 carries a pattern to be checked and the other carries a reference pattern, and these boards are compared to each other. The fine adjustment table 16 attached with a drive motor 24 is movable in the X directions. Similarly, the fine adjustment table 18 attached with a drive motor 26 is movable in the Y directions. Imagers 28 and 30 such as television cameras are arranged above the fine adjustment tables 16 and 18, respectively. Typically, the imagers 28 and 30 are fixed at positions from which these imagers can image corresponding identical positions on the printed circuit boards 20 and 22. Electrically connected to the imagers 28 and 30 are binary circuits 32 and 34 which in turn are connected to data memory circuits 36 and 40, respectively, and to a horizontal bit counter 42, so that output signals from the imagers are converted into binary signals and inputted to the circuits 36 and 40 and counter 42. An output signal from the horizontal bit counter 42 is inputted to a control circuit 44 which controls the data memory circuits 36 and 40 and a defect detector 46 such that output signals from the memory circuits, 36 and 40 are inputted to the defect detector 46. The control circuit 44 also controls the drive motors 12, 14, 24 and 26 so as to effect relative positioning between the two printed circuit boards 20 and 22 which are compared to each other.

The printed circuit boards 20 and 22 are both configured as exemplified in FIG. 2. More particularly, each of the printed circuit boards 20 and 22 has pattern areas 48 and 50. A pattern or patterns formed in the pattern area 48 of the board 20 are identical to a pattern or patterns formed in the pattern area 48 of the board 22. The same relationship is held between corresponding patterns formed in the pattern areas 50 of the boards 20 and 22. The pattern areas 48 and 50, designated by phantom lines, are respectively surrounded by contouring lines 52 and 54 to define areas which are surrounded by an exposed substrate portion 56. This portion 56 is formed by etching. Outside the exposed substrate portion 56, the printed circuit board 20 or 22 has a peripheral marginal portion which is applied with a foil of copper to form a copper foiled portion 60. A plurality of pin holes 62 are formed in the copper foiled portion 60.

To check a pattern with the checking apparatus described previously, the printed circuit boards 20 and 22 are mounted on the fine adjustment tables 16 and 18 having their guide pins (not shown) fitted in the pin holes 62, so as to be positioned and fixed with accuracies of approximately 0.1 to 0.2 mm. Subsequently, registration patterns formed at corresponding predetermined positions on the printed circuit boards 20 and 22 are imaged by the imagers 28 and 30, for example, television cameras. A crucial mark including orthogonal straight line segments as shown in FIG. 7A may be provided for use as the registration mark. However, in fabrication of a product of printed circuit board, it is general practice to prepare a substrate by cutting out from a material plate so that the substrate has a standard size which is larger by one order than a contour size of the product, to form patterns on the substrate through printing and ethcing processes and finally, to dice the substrate to obtain a printed circuit board of the ultimate product contour size. Accordingly, the printed circuit board prior to the final finishing has, at four corners as indicated by dotted circles $P_1$, $P_2$, $P_3$ and $P_4$, patterns each including orthogonal straight line segments as shown in FIG. 7B and these patterns may be used as registration patterns. Any one of the four corners $P_1$ to $P_4$ on each of the printed circuit boards 20 and 22 is imaged by the imager 28 or 30. Examples of corner images imaged by the imagers 28 and 30 are exaggeratedly illustrated in FIGS. 3A and 3B wherein FIG. 3A corresponds to the corner $P_1$ and FIG. 3B to the corner $P_2$. Either corner image includes orthogonal straight line segments 64 and 66 which respectively lie in the X and Y directions shown in FIG. 1.

The output signals of the imagers 28 and 30 are converted into binary video signals by the binary circuits 32 and 34 and inputted to the data memory circuits 36 and 40. Output signals of the memory circuits 36 and 40 are selectively displayed on a display unit (not shown) such as a monitor television. When taking the corner $P_1$, for instance, registration patterns imaged by the imagers 30 and 28 are diagrammatically illustrated in binary form in FIGS. 4A dn 4B, respectively. In these figures, a binary video signal indicative of the copper foiled portion 60 is represented by a logic "0" and a binary video signal indicative of the exposed substrate portion 56 is represented by a logic "1". More particularly, the patterns imaged by the imagers 28 and 30 are selectively displayed as monochromatic pictures on the monitor television not shown. A logic "0" region (copper foiled portion 60) is displayed as a black picture portion and a logic "1" region (exposed substrate portion 56) is displayed as a white picture portion. Conversely, the copper foiled portion 60 may be represented by the logic "1" and the exposed substrate portion 56 by the logic "0".

Figure 4A:
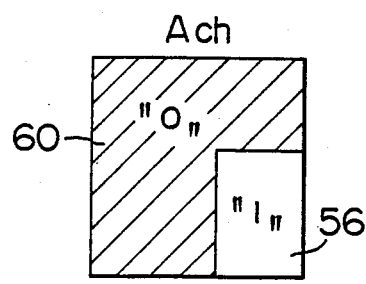
FIGS. 4A and 4B are diagrams showing examples of images displayed on a television monitor.
Figure 4B:
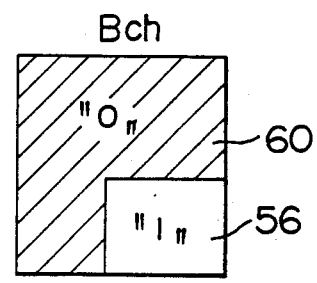
Figure 5A:
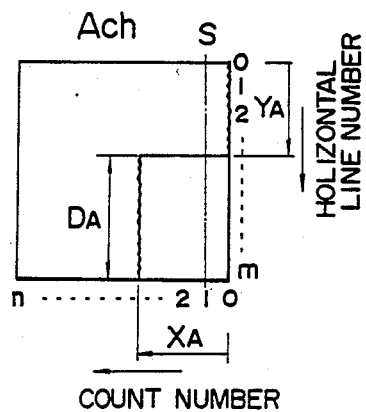
FIGS. 5A and 5B are diagrams showing histograms provided by a control circuit on the basis of output signals from a horizontal bit counter.
Figure 5B:
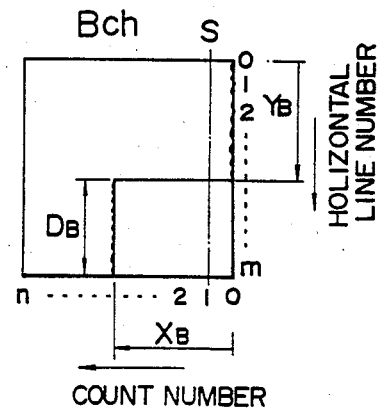

The binary video signals displayed as shown in FIGS. 4A and 4B are bit serial signals which are indicative of the video signals of the imagers 28 and 30 together with horizontal sync signals and vertical sync signals and which are delivered out of the binary circuits 32 and 34. The bit serial signals are inputted to the data memory circuits 36 and 40 and also to the horizontal bit counter 42. The horizontal bit counter 42 accumulates a number of bits of logic "1" associated with each one horizontal line delivered out of either the binary circuit 32 (B channel) or the binary circuit 34 (A channel). Accumulation data pieces are inputted to the control circuit 44. Based on the input accumulation data pieces, the control circuit 44 prepares count histograms as shown in FIGS. 5A and 5B. The count histograms of FIGS. 5A and 5B respectively correspond to the image patterns of FIGS. 4A and 4B and in each histogram, the boundary between the logic "0" region and the logic "1" region is indicated. Specifically, a boundary line in the Y directions occurs on a horizontal line at which the count data changes greatly, and a boundary line in the X directions occurs on a line represntative of an average of effective counts. To avoid inclusion of erroneous data due to external noise, the control circuit 44 applies noise level cutting and data averaging to the accumulation data pieces.

More particularly, assuming that one horizontal line is divided into n bits, one frame is divided into m horizontal lines and a noise cut level is S, the control circuit 44 so handles the number of counts that a count number associated with one horizontal line is recognized as zero when it is smaller than S but recognized as that count number when it exceeds S. The control circuit 44 then measures a horizontal line number (the number of horizontal lines) $D_A$ or $D_B$ with which a count number (the number of counts) exceeding S is associated, and averages counts to provide a count average value $X_A$ or $X_B$. The number of counts changes at the boundary line in the Y directions, designated by $Y_A$, and at the boundary line in the X directions. These boundary lines $Y_A$ and $Y_B$ can be obtained from the following equations:

$$Y_A = m - D_A \quad (1)$$

$$Y_B = m - D_B \quad (2)$$

The thus measured values of $X_A$, $X_B$, $Y_A$ and $Y_B$ are related to each other as diagrammatically shown in FIG. 6 depicting a combined image of the A channel and B channel images. The control circuit 44 then controls the drive motor 24 such that the fine adjustment table 16 is moved by $\Delta X = X_B - X_A$ in the X directions to make $X_B$ equal to $X_A$. At the same time, the control circuit 44 controls the drive motor 26 such that the fine adjustment table 18 is moved by $\Delta Y = Y_B - Y_A$ to make $Y_A$ equal to $Y_B$. As a result, the two registration images are matched. The above positioning adjustment may be repeated to obtain more accurate results.

Subsequently, the control circuit 44 controls the drive motors 12 and 14 such that the XY table 10 is moved to allow the imagers 28 and 30 to image patterns (one being a pattern to be checked and the other being a reference pattern) in the pattern area 48 or 50 or both on the printed circuit boards 20 and 22. Signals representative of the corresponding identical patterns on the boards 20 and 22 imaged by the imagers 28 and 30 are converted into binary signals by the binary circuits 32 and 34 and inputted via the data memory circuits 36 and 40 to the defect detector 46 at which they are compared with each other for judgement of matching or unmatching of the patterns.

As described previously, according to this embodiment, the image registration can be realized with a high accuracy comparable to the finest resolution of the image. Moreover, the corner patterns originally formed on the printed circuit board are used as registration patterns and there is no need of preparing special patterns dedicated to registration. The accurate image registration improves accuracies of the pattern comparison and reliability of the apparatus. In addition, the image registration can be automated to improve operation efficiency.

In place of the registration pattern of FIG. 7B used in the foregoing embodiment, any pattern including the boundaries in the X and Y directions, such as for example a pattern shown in FIG. 7C, may be used as a registration pattern to attain the same effects. In order to match the patterns imaged by the imagers 28 and 30, in the foregoing embodiment, the fine adjustment tables 16 and 18 are operated. But for matching of the patterns, the imagers 28 and 30 may be moved by means of motors not shown. For example, registration in the X directions may be effected by the fine adjustment table and registration in the Y directions may be effected by moving the imager. Although in the embodiment of FIG. 1 the fine adjustment table 16 is movable only in the X directions and the fine adjustment table 18 is movable only in the Y directions, each of the fine adjustment tables 16 and 18 may obviously be designed so as to be independently movable in the X and Y directions.

We claim:

1. An apparatus for checking patterns on printed circuit boards comprising:
    inspection table means for fixing thereon at least two printed circuit boards on which patterns to be compared with each other are formed;
    imager means for imaging the respective patterns on the respective printed circuit boards;
    display means for displaying images of the patterns imaged by said imager means; and
    comparing means for comparing said images of the patterns,
    said printed circuit boards each having registration patterns each including orthogonal straight line segments,
    said apparatus further comprising registration means for matching images of the registration patterns formed on the respective printed circuit boards and displayed on said display means.

2. A pattern checking apparatus according to claim 1 wherein said imager means comprises binary circuits, and the images of the registration patterns are displayed in binary form on said display means.

3. A pattern checking apparatus according to claim 1 wherein said registration pattern comprises boundary lines between a copper foiled portion and an exposed substrate portion of said printed circuit board.

4. A pattern checking apparatus according to claim 3 wherein said imager means comprises binary circuits, and the images of the registration patterns are displayed in binary form on said display means.

5. A pattern checking apparatus according to claim 1 wherein said inspection table means comprises two auxiliary tables for independently moving the respective printed circuit boards in a plane, and said registration means comprises drive motors for moving said auxiliary tables.

6. A pattern checking apparatus according to claim 5 wherein said imager means comprises binary circuits, and the images of the registration patterns are displayed in binary form on said display means.

7. A pattern checking apparatus according to claim 5 wherein said registration pattern comprises boundary lines between a copper foiled portion and an exposed substrate portion of said printed circuit board.

8. A pattern checking apparatus according to claim 7 wherein said imager means comprises binary circuits, and the images of the registration patterns are displayed in binary form on said display means.

9. A pattern checking apparatus according to claim 1 wherein said registration means comprises drive motors for moving said imager means in a plane.

10. A pattern checking apparatus according to claim 9 wherein said imager means comprises binary circuits, and the images of the registration patterns are displayed in binary form on said display means.

11. A pattern checking apparatus according to claim 9 wherein said registration pattern comprises boundary lines between a copper foiled portion and an exposed substrate portion of said printed circuit board.

12. A pattern checking apparatus according to claim 11 wherein said imager means comprises binary circuits and the images of the registration patterns are displayed in binary form on said display means.

* * * * *